United States Patent
Hada et al.

(10) Patent No.: US 7,445,698 B2
(45) Date of Patent: Nov. 4, 2008

(54) GAS CONCENTRATION DETECTING APPARATUS

(75) Inventors: Satoshi Hada, Inazawa (JP); Tomoo Kawase, Aichi-ken (JP); Eiichi Kurokawa, Okazaki (JP)

(73) Assignee: DENSO Corporation, Kariya (JP)

( * ) Notice: Subject to any disclaimer, the term of this patent is extended or adjusted under 35 U.S.C. 154(b) by 771 days.

(21) Appl. No.: 10/813,442

(22) Filed: Mar. 31, 2004

(65) Prior Publication Data

US 2004/0217001 A1 Nov. 4, 2004

(30) Foreign Application Priority Data

Mar. 31, 2003 (JP) ............................. 2003-096375
Feb. 17, 2004 (JP) ............................. 2004-039566

(51) Int. Cl.
*G01N 27/409* (2006.01)
*G01N 27/41* (2006.01)

(52) U.S. Cl. ....................... 204/401; 204/406; 204/426; 73/23.32

(58) Field of Classification Search ................. 204/425, 204/426; 205/783.5; 73/23.32
See application file for complete search history.

(56) References Cited

U.S. PATENT DOCUMENTS

| 5,709,198 A | 1/1998 | Sagisaka et al. |
| 6,009,866 A | 1/2000 | Sagisaka et al. |
| 6,136,169 A * | 10/2000 | Okamoto .................... 204/401 |
| 6,314,790 B1 | 11/2001 | Sagisaka et al. |
| 6,347,544 B1 * | 2/2002 | Hada et al. ................. 73/23.32 |

FOREIGN PATENT DOCUMENTS

| JP | 8-271475 | 10/1996 |
| JP | 2000-121600 | 4/2000 |

OTHER PUBLICATIONS

Japanese Office Action mailed Aug. 28, 2007 in Japanese Appln. No. 2004-039566 with English translation.

* cited by examiner

*Primary Examiner*—Kaj K Olsen
(74) *Attorney, Agent, or Firm*—Nixon & Vanderhye PC

(57) ABSTRACT

In a gas concentration detecting apparatus, a voltage is applied to electrodes of a sensor element. A change is caused in either the applied voltage or an element current. An amount of a change in each of a current value and a voltage value caused is measured in response to the caused change. An amount of resistance of the sensor element is calculated based on a ratio between the change amounts in the current value and the voltage value. A detection unit detects abnormality relating to controlling the sensor by utilizing at least one of the change amounts in the current value and the voltage value.

9 Claims, 13 Drawing Sheets

GAS CONCENTRATION DETECTING APPARATUS

BACKGROUND OF THE INVENTION

1. Field of the Invention

The present invention relates to a gas concentration detecting apparatus for detecting a specific component concentration based on detection results from a gas concentration sensor and, more particularly, to an improved technique for suitably detecting abnormality in a sensor control system.

2. Description of the Related Art

One known gas concentration sensor is, for example, a limiting-current type air-fuel ratio sensor (referred to as A/F sensor), which takes an exhaust gas released from a vehicle engine as a detected gas and detects the oxygen concentration (air-fuel ratio) in the exhaust gas. Specifically, the A/F sensor has a sensor element that includes a solid electrolyte member and a pair of electrodes disposed on that solid electrolyte member. The A/F sensor is configured to flow an element current corresponding to the present concentration, which is caused by an applied voltage on the sensor element. The A/F sensor then measures the element current flow through the sensor element to detect the oxygen concentration (air-fuel ratio).

The above-described A/F sensor cannot accurately measure the element current or cannot detect the oxygen concentration (air-fuel ratio), if any abnormality occurs at the sensor element terminals, such as a short to the power supply (power supply short circuit), a short to the ground (GND short circuit), and a short across the terminals (terminal-to-terminal short circuit). The conventional A/F sensors, therefore, use the voltages at both terminals of the sensor element as an A/D input for a microcomputer, and detect the abnormality if the A/D input is out of a predetermined range. Receiving voltages at both terminals of the sensor to obtain an A/D input needs, however, extra A/D converters by the number of the sensor terminals. This configuration is very complicated. An improved technique is thus required.

The conventional technique shown in a Japanese application patent laid-open publication No. HEI 08 (1996)-271475, for example, monitors the A/F sensor activation state to detect a sensor abnormality. Specifically, the A/F sensor abnormality is detected by determining whether the A/F sensor element resistance detected is in a predetermined range, or by determining whether the power supply to the heater for element activation is in a predetermined range. That is, the sensor abnormality is detected by determining whether the sensor element is normally activated.

The above-described abnormality detection method in the Japanese application patent laid-open publication, however, determines the state where the sensor element should obviously be activated and detects the sensor element abnormality if the sensor element is not activated under the state. The method can thus precisely detect the abnormality only under the state where the sensor element is actually activated or the state where the sensor element can be definitely determined to be activated. This then places much restriction on the sensor element abnormality detection. The method for sensor element abnormality detection based on the power supply to the heater needs circuitry for measuring the heater power or A/D converter or the like. This makes it hard to simplify the configuration. These problems need more preferable technique for detecting abnormality in the sensor control system.

SUMMARY OF THE INVENTION

The present invention was accomplished in light of the abovementioned circumstances. An object of the present invention is to provide a gas concentration detecting apparatus that is able to suitably detect abnormality in relation to various circuits incorporated in the apparatus, without causing the configuration of the apparatus to be more complicated.

In order to achieve the above object, as one aspect of the present invention, there is provided a gas concentration detecting apparatus applied to a gas concentration sensor including a sensor element sensing a concentration of a gas to be detected, the sensor element being equipped with a solid electrolyte member and one or more pairs of electrodes disposed on the solid electrolyte member, the apparatus comprises a control unit configured to control a voltage applied to at least one of positive and negative terminals connected to the electrodes of the sensor element; a measurement unit configured to measure either an element current flow caused by the applied voltage corresponding to a concentration of a specific component of the gas, every time when the voltage is applied under the control of the applied voltage, or an electromotive force generated between the electrodes of the sensor element corresponding to the concentration of the specific component of the gas, every time when the voltage is applied under the control of the applied voltage; a change causing unit configured to cause a change in either the applied voltage to the sensor element or the element current through the sensor element; a change amount measuring unit configured to measure an amount of a change in each of a current value and a voltage value caused in response to the change caused in either the applied voltage or the element current; a calculation unit configured to calculate an amount of a resistance component to resist the element current flow through the sensor element on the basis of a ratio between the amounts of the changes in the current value and the voltage value; and a detection unit configured to detect abnormality relating to controlling the sensor by utilizing information relating to calculating the amount of the resistance component calculated by the calculation unit.

Hence, during the calculation of the element resistance, no change of the element current responds to the change added to the applied voltage on the sensor element so that no change of the element current can be monitored, for example, if any abnormality occurs in the sensor control system, such as the power supply short circuit or the GND short circuit at one or more of the positive and negative terminals of the sensor element, or the terminal-to-terminal short circuit across the positive and negative terminals. If the change is added to the element current instead of the applied voltage, no change of the applied voltage will respond to the change of the current so that no change of the applied voltage can be monitored. By determining whether no change of current or voltage responds to the change of the applied voltage or current, therefore, one method for abnormality detection can suitably detect the abnormality in the sensor control system, such as the power supply short circuit, the GND short circuit, the terminal-to-terminal short circuit, or the disconnection. The above-described abnormality detection method detects the abnormality with the measured data (current variation, or voltage variation) for use in the element resistance calculation. No additional A/D converter (A/D input for the microcomputer) is thus needed for the abnormality detection, thereby preventing the need for using a complicated configuration.

One technique for calculating the element resistance with the change added to the applied voltage or current of the sensor element is an element resistance calculation method by the so-called sweeping method. This method calculates the element resistance based on the variation of the current or voltage caused by temporally changing the applied voltage or current of the sensor element. It is known that this calculation method needs no modification of the applied voltage on the sensor into the resistance-dominant region of a V-I characteristics, thereby reducing the no-detection time of the gas concentration. The applied voltage or current of the sensor element can also be alternately or continuously changed to add change to that applied voltage or current. The element resistance can also be calculated as element admittance in addition to the element impedance. The admittance is the inverse of the element impedance.

Preferably, the information relating to calculating the amount of the resistance component is at least one of the amounts of the changes in the current value and the voltage value and the detection unit is provided with a monitor unit configured to monitor the amount of the change in either the current value or the voltage value, the amount of the change being measured by the measurement unit; and a determination unit configured to determine the abnormality on the basis of the amount of the change monitored by the monitor unit.

It is preferred that the determination unit is configured to determine that there occurs the abnormality, when the amount of the change in either the current value or the voltage value is equal to zero or a value substantially regarded as zero.

It is also preferred that the information relating to calculating the amount of the resistance component is the amount of the resistance component itself and the detection unit is configured to detect the abnormality on the basis of the amount of the resistance component itself.

It is also preferred that the change amount measuring unit includes an operated amount measuring unit configured to measure an actually operated amount of either the applied voltage or the sensor current obtained when the change is caused in the either the applied voltage or the sensor current, the actually operated amount serving as the information relating to calculating the amount of the resistance component and serving as the amount of the change in one of the current value and the voltage value and the detection unit is configured to detect the abnormality with reference to the actually operated amount.

The resistance component to resist the element current flow through the sensor element is one of an impedance and an admittance of the sensor element.

As another aspect of the present invention, there is a gas concentration detecting apparatus applied to a gas concentration sensor including a sensor element sensing a concentration of a gas to be detected, the sensor element being equipped with a solid electrolyte member and one or more pairs of electrodes disposed on the solid electrolyte member. The apparatus comprises a control unit configured to control a voltage applied to at least one of positive and negative terminals connected to the electrodes of the sensor element; a measurement unit configured to measure either an element current flow caused by the applied voltage corresponding to a concentration of a specific component of the gas, every time when the voltage is applied under the control of the applied voltage, or an electromotive force generated between the electrodes of the sensor element corresponding to the concentration of the specific component of the gas, every time when the voltage is applied under the control of the applied voltage; a change causing unit configured to cause a change in either the applied voltage to the sensor element or the element current through the sensor element; a change amount acquiring unit configured to acquire an amount of a change in at least one of a current value and a voltage value caused in response to the change caused in either the applied voltage or the element current; and a detection unit configured to detect abnormality relating to controlling the sensor by utilizing information relating to the amount of the change acquired by the change amount acquiring unit.

One preferred example is that the change amount acquiring unit is composed of a change amount measuring unit configured to measure the amount of the change in at least one of the current value and the a voltage value caused in response to the change caused in either the applied voltage or the element current.

BRIEF DESCRIPTION OF THE DRAWINGS

Other objects and aspects of the present invention will become apparent from the following description and embodiments with reference to the accompanying drawings in which.

DETAILED DESCRIPTION OF THE PREFERRED EMBODIMENTS

Referring to the accompanying drawings, preferred embodiments of the present invention will now be described.

First Embodiment

Referring to FIGS. 1 to 6, a first embodiment of the present embodiment will now be described.

In the present embodiment, an air-fuel ratio detecting apparatus is embodied, which takes in an exhaust gas (combustion gas) released from a vehicle engine as a detected gas and detects oxygen concentration (air-fuel ratio, hereinafter also referred to as A/F) in the gas. The air-fuel ratio control system including an engine ECU or the like uses the detection results of the air-fuel ratio. The air-fuel ratio control system adequately uses combustion controls such as a stoichiometry combustion control for feedback controlling the air-fuel ratio near the stoichiometry and a lean combustion control for feedback controlling the air-fuel ratio in a predetermined lean area.

Figure 1:
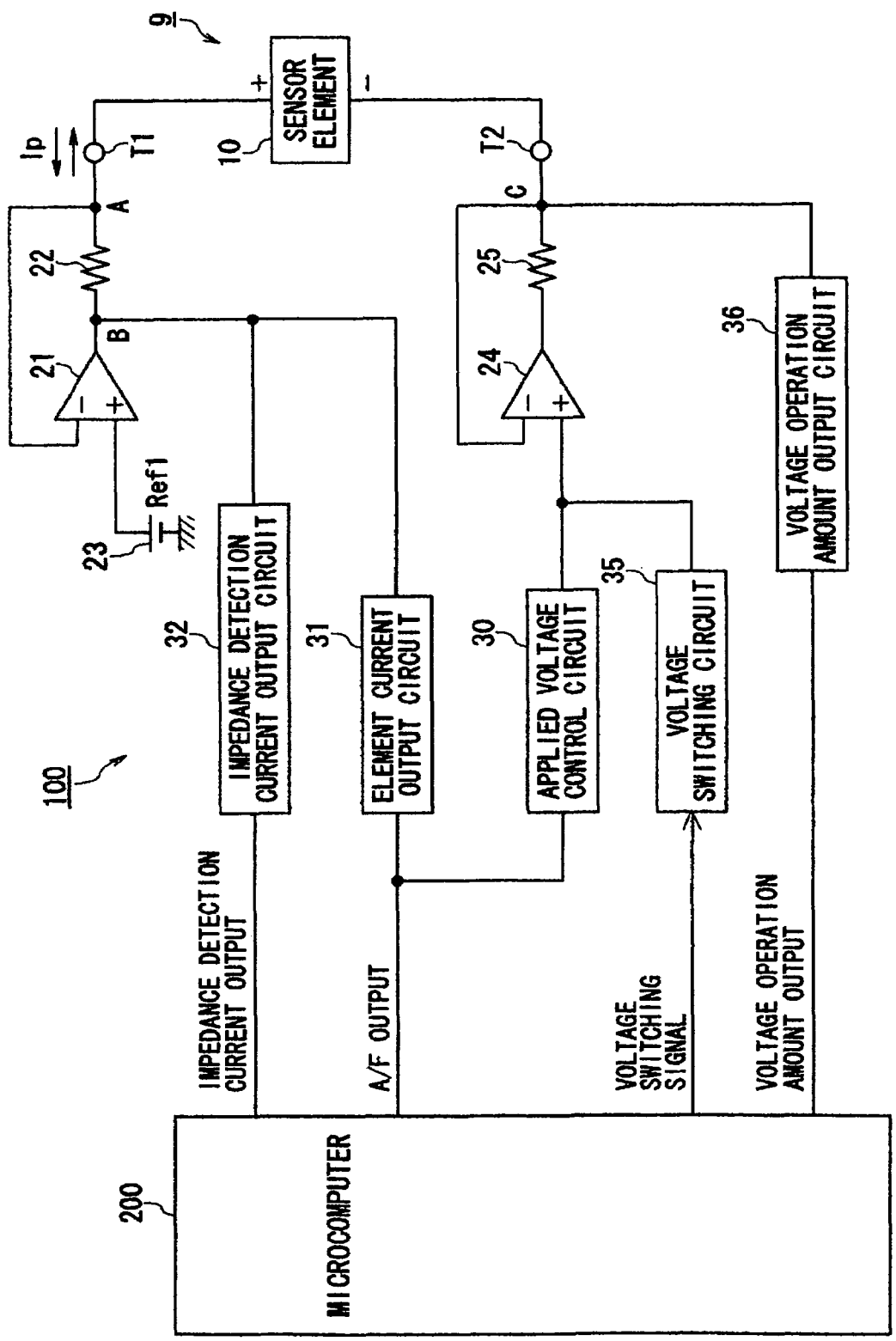
FIG. 1 shows a block diagram of a sensor control circuit in an embodiment according to the present invention.
Figure 2:
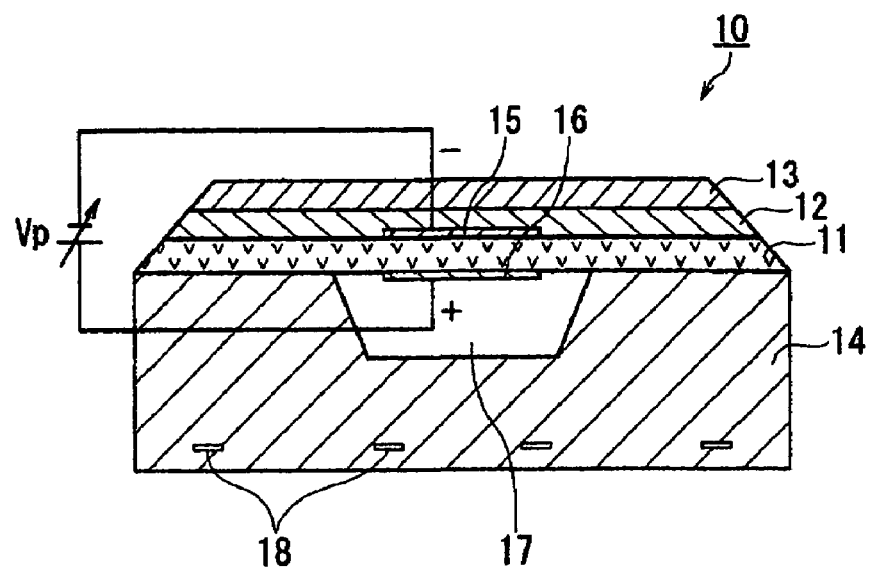
FIG. 2 shows a cross-sectional view of the configuration of a sensor element.

FIG. 1 shows the configuration of the air-fuel ratio detecting apparatus including a sensor control circuit, while FIG. 2 shows the configuration of the A/F sensor.

First, with reference to FIG. 2, the A/F sensor which serves as a gas concentration sensor will be described below.

The A/F sensor includes a sensor element 10 of a laminated structure. FIG. 2 shows the cross-sectional configuration of the sensor element 10. The sensor element 10 actually forms a long length that extends perpendicularly to the plane of FIG. 2. The whole element resides in a housing or an element cover.

The sensor element 10 includes a solid electrolyte 11, a diffusion resistance layer 12, a shielding layer 13, and an insulating layer 14. These are laminated vertically in FIG. 2. A protective layer (not shown) covers the element 10. The solid electrolyte 11 (solid electrolyte member) of a rectangular plate is a sheet of partially stabilized zirconia. The solid electrolyte 11 includes a pair of electrodes 15, 16 opposed on each side of it. The electrodes 15, 16 are made of such as platinum Pt. The diffusion resistance layer 12 includes a porous sheet for introducing the exhaust gas to the electrode 15. The shielding layer 13 includes a dense layer for restraining the transmission of the exhaust gas. These layers 12, 13 both include a sheet of ceramic such as alumina, zirconia, formed such as by sheet forming techniques. The layers have different gas permeability due to different average pore size of porosity and different porosity.

The insulating layer 14 includes ceramic such as alumina, zirconia. The layer 14 includes an atmosphere duct 17 in a region facing the electrode 16. The insulating layer 14 also includes embedded heaters 18 made of such as platinum Pt. The heaters 18 include a linear heating element that generates heat by electricity from the battery power supply to heat the whole sensor element. The electrode 15 may also be referred to as a diffusion-layer-side electrode and the electrode 16 may also be referred to as an atmosphere-side electrode in the description below, if required. In this embodiment, it is assumed that the terminal connected to the atmosphere-side electrode 16 is a positive terminal (+ terminal), and the terminal connected to the diffusion-layer-side electrode 15 is a negative electrode (− terminal).

In the sensor element 10 described above, the surrounding exhaust gas enters the diffusion resistance layer 12 through its side region to reach the diffusion-layer-side electrode 15. For a lean exhaust gas, the voltage applied across electrodes 15 and 16 will decompose and ionize the oxygen in the gas at the diffusion-layer-side electrode 15. The ionized oxygen will then pass through the solid electrolyte 11 before escaping through the atmosphere-side electrode 16 into the atmosphere duct 17. This can flow a current (positive current) in a direction from the atmosphere-side electrode 16 to the diffusion-layer-side electrode 15. For a rich exhaust gas, in contrast, the voltage will decompose and ionize the oxygen in the atmosphere duct 17 at the atmosphere-side electrode 16. The ionized oxygen will then pass through the solid electrolyte 11 before escaping through the diffusion-layer-side electrode 15. The oxygen will then react catalytically with unburned components, such as HC or CO, in the exhaust gas. This can flow a current (negative current) in a direction from the diffusion-layer-side electrode 15 to the atmosphere-side electrode 16.

Figure 3:
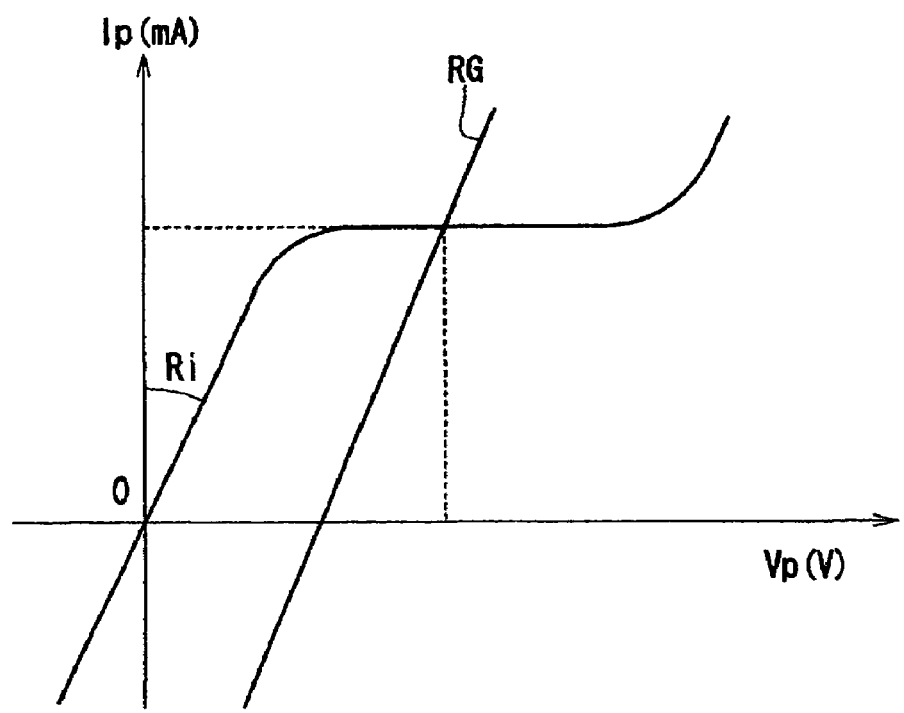
FIG. 3 shows output characteristics of an A/F sensor.

FIG. 3 shows fundamental voltage-current characteristics ("V-I" characteristics) on the A/F sensor. In FIG. 3, the flat part parallel to the voltage axis (horizontal axis) is a limiting-current region which specifies the element current Ip (limiting current) of the sensor element 10. The increase and decrease of this element current Ip correspond to the increase and decrease of the air-fuel ratio (i.e., the degree of lean or rich). That is, an air-fuel ratio closer to the lean side can cause more element current Ip, while an air-fuel ratio closer to the rich side can cause less element current Ip.

In the "V-I" characteristics, the lower voltage side than the limiting-current region is a resistance-dominant region. The DC internal resistance Ri of the sensor element 10 specifies the slope of the first-order straight-line part in the resistance-dominant region. The DC internal resistance Ri varies with the element temperature. A lower element temperature causes a higher DC internal resistance Ri. This thus provides a smaller slope of the first-order straight-line part (the straight-line part lies) in the resistance-dominant region. A higher element temperature causes a lower DC current internal resistance Ri. This thus provides a larger slope of the first-order straight-line part (the straight-line part rises) in the resistance-dominant region. A line RG in FIG. 3 shows applied voltage characteristics (applied voltage line) for determining the applied voltage Vp on the sensor element 10.

FIG. 1 shows an electrical circuit diagram of the configuration of the sensor control circuit 100. In FIG. 1, the + terminal T1 connects to the atmosphere-side electrode 16 of the sensor element 10. A reference power supply 23 connects to the + terminal T1 through an operational amplifier 21 and a current detection resistance 22, as shown in FIG. 1. The − terminal T2 connects to the diffusion-layer-side electrode 15 of the sensor element 10. An applied voltage control circuit 30 connects to the − terminal T2 through an operational amplifier 24 and a resistance 25. The operational amplifiers 21, 24 correspond to the "feedback amplification circuits." Point A at one end of the current detection resistance 22 is kept at the same voltage as the reference voltage Ref 1. The element current Ip flows through the current detection resistance 22. The voltage at point B varies with the element current Ip. For a lean exhaust gas, the element current Ip flows through the sensor element 10 from the + terminal T1 to the − terminal T2 to increase the point B voltage. In contrast, for a rich exhaust gas, the element current Ip flows through the sensor element 10 from the − terminal T2 to the + terminal T1 to decrease the point B voltage. This point B voltage is output as the A/F output of the detection result of the air-fuel ratio to the microcomputer 200 through the element current output circuit 31. The microcomputer 200 A/D receives and converts the A/F output. The element current output circuit 31 includes, for example, an S/H (sample/hold) circuit. The circuit samples the point B voltage during the detection of the air-fuel ratio, and sequentially updates and outputs the sampled value during a predetermined gate-on period. This A/F output can adequately be used for feedback control or the air-fuel ratio and the like.

The applied voltage control circuit 30 monitors the A/F output (sample-hold value of the point B voltage) and determines the voltage to be applied on the sensor element 10 corresponding to the output. As with the applied voltage characteristics RG shown in FIG. 3, the circuit 30 basically controls the applied voltage in such a way that the voltage increases if the element current Ip increases (i.e., the point B voltage increases).

The air-fuel ratio detection apparatus uses the so-called sweeping method to detect the element impedance of the sensor element 10. Specifically, the voltage switching circuit 35 alternately changes the voltage applied on the sensor in response to the voltage-switching signal from the microcomputer 200. The microcomputer 200 regularly outputs the voltage-switching signal to the voltage switching circuit 35. For example, every 128 msec, the circuit 35 can temporally switch the applied voltage on the sensor from the usual applied voltage for the air-fuel ratio detection (controlled voltage by the applied voltage control circuit 30) to the applied voltage for the impedance detection.

In this case, the point B corresponds to a "variation measurement portion." The point B voltage is output as the impedance detection current output to the microcomputer 200 through the impedance detection current output circuit 32. The microcomputer 200 receives the impedance detection current output and A/D converts it. The impedance detection current output circuit 32 includes, for example, an HPF (high pass filter) circuit and a P/H (peak hold) circuit that are connected in series. These HPF and P/H circuits can measure the alternating current variation at the point B during a predetermined gate-on period that corresponds to the impedance detection period. The peak-hold point B voltage can be reset every gate off.

The point C voltage in FIG. 1 is the same voltage as the output voltage of the applied voltage control circuit 30 or the voltage switching circuit 35. The point C voltage is output as the voltage operation amount output to the microcomputer 200 through the voltage operation amount output circuit 36. The microcomputer 200 receives the voltage operation amount output and A/D converts it. The voltage operation amount output circuit 36 includes, for example, an HPF circuit and a P/H circuit that are connected in series. The point C corresponds to an "operation amount measurement portion." The microcomputer 200 thus detects and receives, as the variation of the alternating voltage at the point C, the variation of the applied voltage on the sensor (the voltage operation amount $\Delta V$ as the actual operation amount) caused by the voltage switching circuit 35, during the detection of the impedance.

The microcomputer 200 calculates the element impedance based on the alternating voltage variation and the induced variation of the element current Ip during the detection of the impedance. The microcomputer 200 controls the electricity to the heater 18 to maintain the element impedance at a predetermined desired value. This is able to keep the sensor element 10 at a certain desired temperature (e.g., 750 degrees C.).

This embodiment detects the abnormality in the sensor control system from the current variation, voltage operation amount, or the like that is obtained during the detection of the element impedance. The abnormality detection procedure will be described below. The abnormality in the sensor control system may include the power supply short circuit or GND short circuit at the + terminal T1 or − terminal T2 of the sensor element 10, the terminal-to-terminal short circuit across the + terminal T1 and − terminal T2, and the disconnection. The method for detecting abnormality in this embodiment is able to detect any of the above-described abnormalities.

Figure 4:
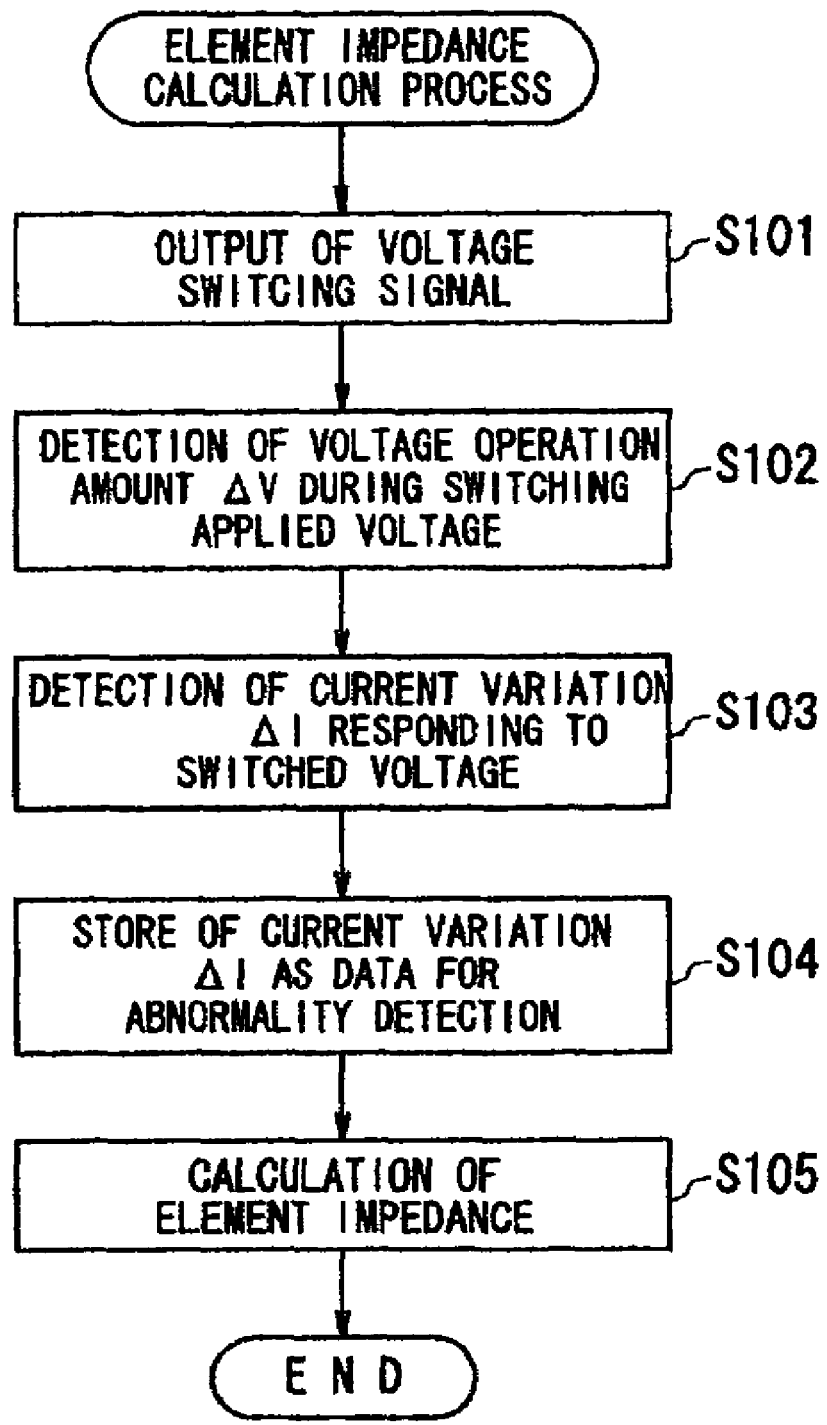
FIG. 4 shows a flowchart of a calculation process of the element impedance.

Referring now to flowcharts in FIGS. 4 and 5, the element impedance calculation procedure and abnormality detection procedure performed by the microcomputer 200 will be described. FIG. 4 shows a flowchart of the element impedance calculation process. The microcomputer performs this process every predetermined period (e.g., every 128 msec).

In FIG. 4, step S101 outputs the voltage-switching signal to the voltage switching circuit 35 of the sensor control circuit 100. After receiving this voltage-switching signal, the sensor control circuit 100 alternately switches the applied voltage on the sensor from the voltage at the time for the air-fuel ratio detection to the voltage for the impedance detection. The alternating frequency for switching the applied voltage is, for example, in the range of about 1 kHz to 20 kHz. Step S102 then detects the voltage operation amount $\Delta V$ during switching the applied voltage. The next step S103 detects the element current variation $\Delta I$ responding to the applied voltage switching.

Figure 6:
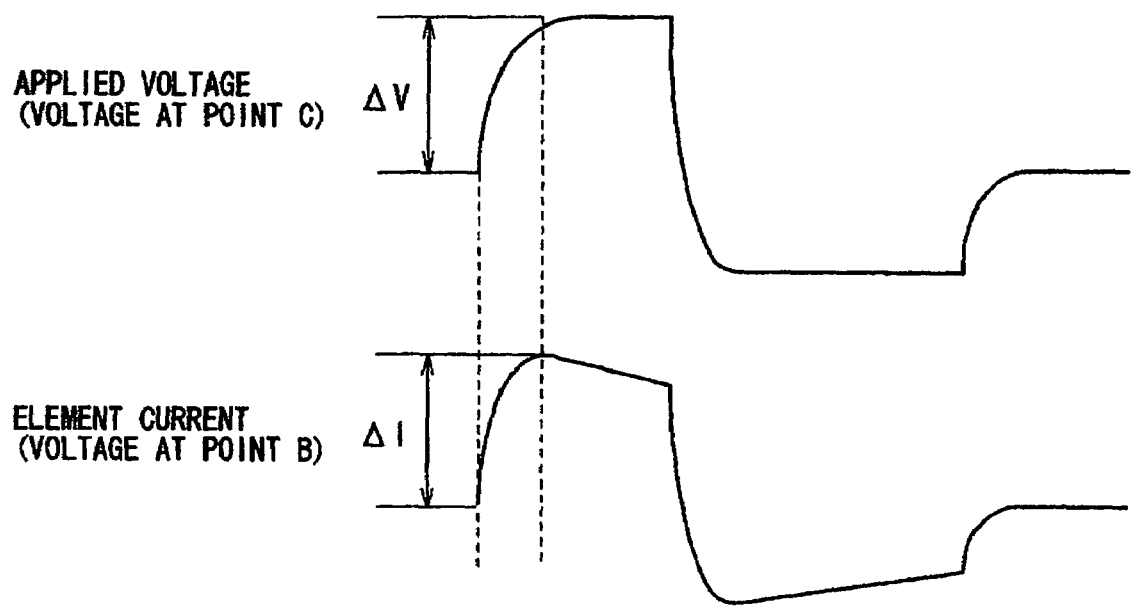
FIG. 6 shows a time chart of applied voltage switching and induced variation of the element current.

In this case, as shown in FIG. 6, the alternating variation is added to the applied voltage on the sensor. In response to this alternating voltage variation, the element current changes. The above-described step S102 detects the voltage operation amount $\Delta V$ based on the point C voltage (voltage operation amount output) that is input to the microcomputer 200 through the voltage operation amount output circuit 36 as shown in FIG. 1. The above-described step S103 detects the current variation $\Delta I$ based on the point B voltage (impedance detection current output) that is input to the microcomputer 200 through the impedance detection current output circuit 32 as shown in FIG. 1.

Step S104 then stores the current variation $\Delta I$ detected in the above-described step S103 in a memory such as RAM as the data for abnormality detection. Step S105 calculates the element impedance from the above-described detected voltage operation amount $\Delta V$ and current variation $\Delta I$ (element impedance=$\Delta V/\Delta I$). The voltage switching circuit 35 as a switching instruction means instructs a predetermined voltage variation. The voltage variation from the voltage switching circuit 35 can thus replace the voltage operation amount $\Delta V$ to calculate the element impedance. In addition to the element impedance, an element admittance, which is the inverse of the element impedance, can be calculated as the element resistance.

Figure 5:
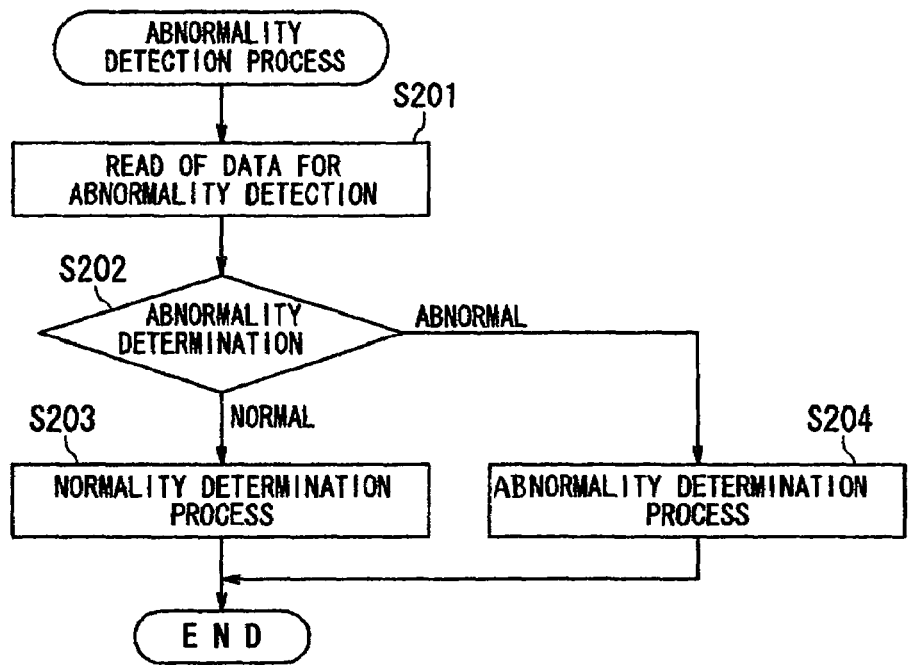
FIG. 5 shows a flowchart of an abnormality detection process.

FIG. 5 shows a flowchart of the abnormality detection process. The microcomputer 200 successively performs this process after the process in FIG. 4.

In FIG. 5, at step S201, the microcomputer 200 reads the current variation $\Delta I$ stored as the data for abnormality detection at the above-described step S104 in FIG. 4. At Step S202, the microcomputer 200 then detects the presence or absence of any abnormality in the sensor control system based on the above-described read current variation $\Delta I$. If the current variation $\Delta I$ is in a predetermined range, the sensor control system is determined to be normal (step S203). If the current variation $\Delta I$ is not in a predetermined range, the sensor control system is determined to be abnormal (step S204). If, for example, the current variation $\Delta I$ is zero or near zero, the sensor control system is determined to be abnormal.

Specifically, if, for example, the + terminal T1 of the sensor element 10 is short-circuited to the power supply, the current flow from the battery power supply to the operational amplifier 21 places the amplifier 21 in the current saturation state. This makes the element current through the current detection resistance 22 a fixed current that is limited by the circuitry. The alternating change of the applied voltage on the sensor thus cannot cause the responsive change of the point B voltage. The current variation $\Delta I$ is therefore near zero, which allows an abnormal state to be determined. The fixed current that is limited by the circuitry is a current that is limited by the output limiting function of the operational amplifier 21. In addition, an additional current-limiting circuit or the output capacity of the output element (e.g., transistor) can also limit the output. A simple incorporation of resistance results in limiting the output.

If the + terminal T1 of the sensor element 10 is short-circuited to the GND, the element current through the current detection resistance 22 is again a fixed current. The alternating change of the applied voltage on the sensor thus cannot cause the responsive change of the point B voltage. The current variation $\Delta I$ is again therefore near zero, which allows the determination of the abnormality occurrence. The alternating change of the applied voltage on the sensor also cannot cause the responsive change of the point B voltage, if the − terminal T2 of the sensor element 10 is short-circuited to the power supply or GND, the + terminal T1 and − terminal T2 are short-circuited between them, or the wires to each of the terminal T1 and T2 are disconnected. The current variation $\Delta I$ is again therefore near zero, which allows the determination of the abnormality occurrence. The abnormality in the sensor control system can thus be detected in any of the cases described above. It should be noted that the abnormality in the sensor element 10 itself could also be detected.

According to the embodiment as described above in detail, the measurement data (current variation) for use in the element impedance detection allows the abnormality detection in the sensor control system, so that the abnormality detection needs no additional A/D converter (A/D input for the microcomputer), thereby preventing the more complicated configuration. The abnormality can also be detected regardless of the activation state of the sensor element 10, so that the abnormality can start to be detected immediately after the A/F sensor starts, before the sensor element 10 is activated. The actually-sufficient condition makes it possible to measure the element impedance (the waiting time may be about several seconds at most), so that the waiting time before the abnormality detection starts can be significantly saved.

Second Embodiment

Figure 7:
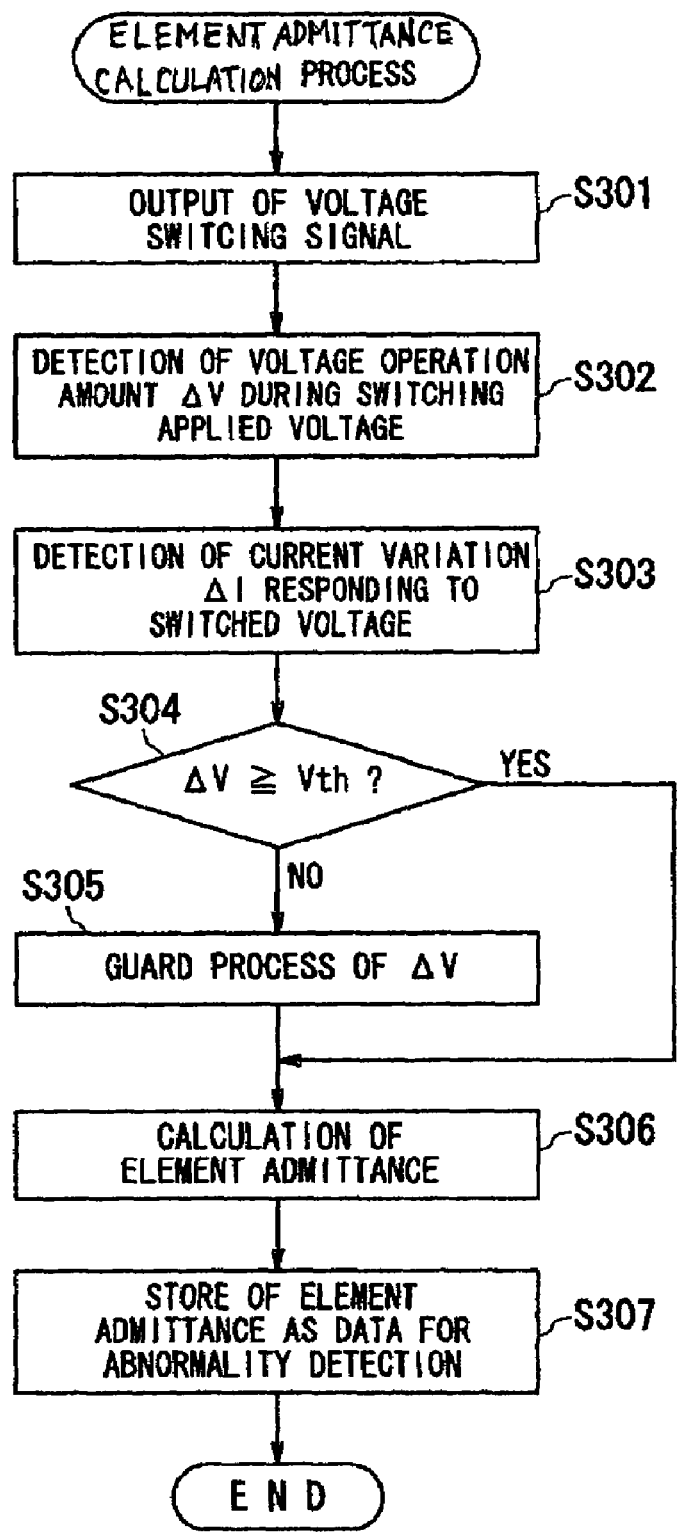
FIG. 7 shows a flowchart of a calculation process of the element admittance in the second embodiment.
Figure 8:
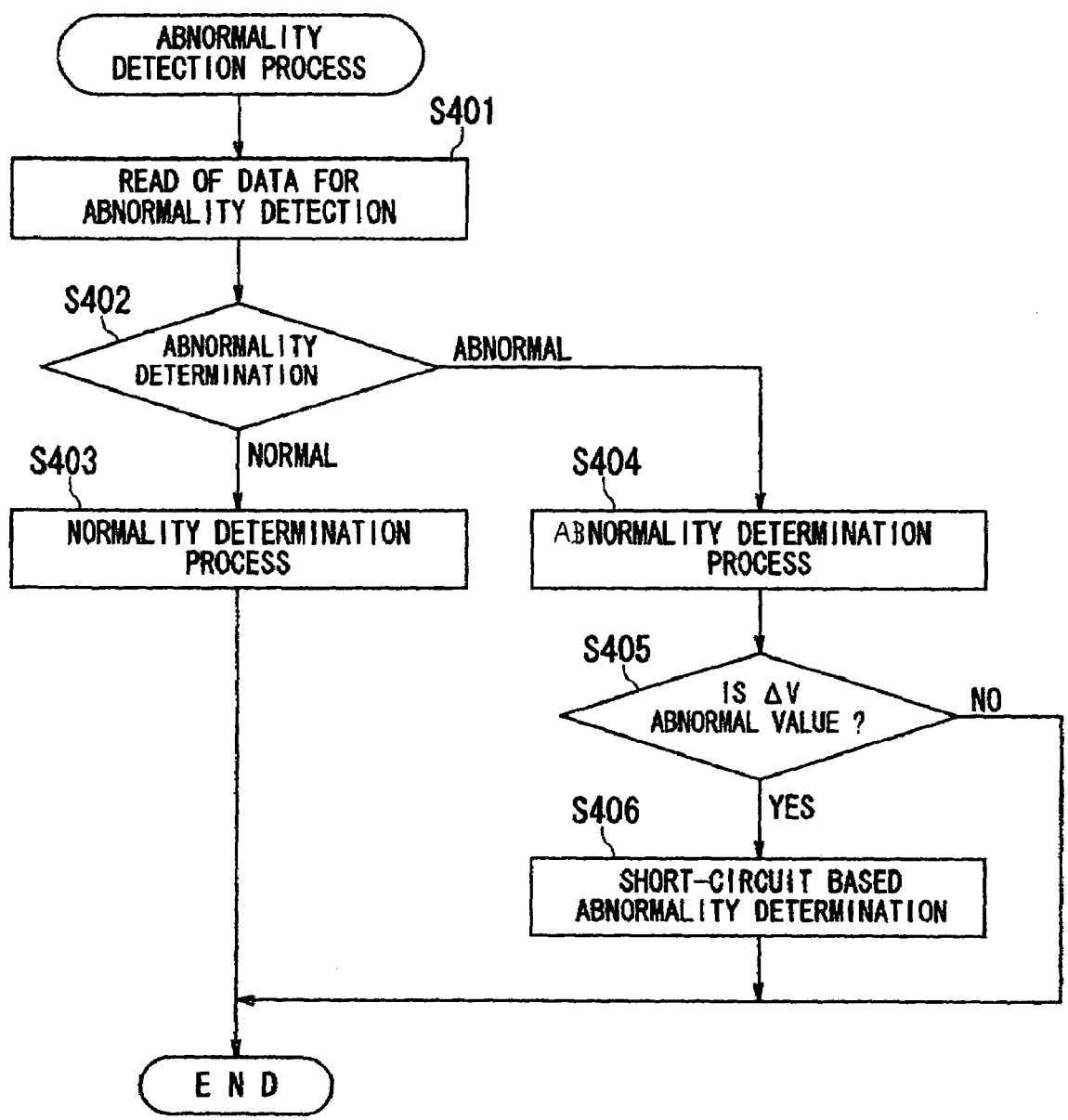
FIG. 8 shows a flowchart of an abnormality detection process in the second embodiment.

Referring to FIGS. 7 and 8, a second embodiment of the present invention will now be described.

The second embodiment according to the present invention will now be described, with an emphasis on the differences from the above-described first embodiment. The first embodiment uses as the data for abnormality detection the current variation $\Delta I$ (impedance detection current output) responding to the switching of the applied voltage to the sensor.

In contrast, the second embodiment uses the calculated value of the element admittance (element admittance=$\Delta I/\Delta V$) as the data for abnormality detection. In short, no current responds to the applied voltage change, or no normal calculated value of the element admittance is provided, during the detection of the element admittance, if any abnormality occurs in the sensor control system, such as the power supply short circuit or the GND short circuit at at least one of the + and − terminals of the sensor element 10, or the terminal-to-terminal short circuit across the positive and negative terminals. This can thus detect the abnormality in the sensor control system. In other words, the current variation $\Delta I$ is zero or near zero if any abnormality occurs, so that the calculated value of the element admittance that is higher than a specified value can provide determination of the abnormality occurrence.

If, for example, at least one of the + and − terminals of the sensor element 10 is short-circuited to the power supply, the voltage operation amount $\Delta V$ is an abnormal value (zero or near zero). The direct use of this abnormal value may not allow the calculation of the element admittance or may give a too large calculated value. This embodiment then replaces the voltage operation amount $\Delta V$ with a predetermined value (not zero) to make it possible to calculate the element admittance, if the voltage operation amount $\Delta V$, which is output by the voltage operation amount output circuit 36, is an abnormal value. The calculated value of the element admittance is then used as the basis to detect the abnormality in the sensor control system. Particularly, if a predetermined value replaces the voltage operation amount $\Delta V$, the voltage operation amount $\Delta V$ is also an abnormal value, so that the abnormality can be specified as the power supply short circuit or the GND short circuit at either one of the + terminal T1 or the − terminal T2 of the sensor element 10.

FIG. 7 shows a flowchart of the element admittance calculation process in this embodiment. This process will replace the process shown in FIG. 4.

In FIG. 7, the processing at steps S301 to S303 makes it possible to output the voltage-switching signal, detect the voltage operation amount $\Delta V$ during switching the applied voltage, and detect the element current variation $\Delta I$ responding to the applied voltage switching, respectively, as in the above-described steps S101 to S103 in FIG. 4.

Step S304 then determines whether the voltage operation amount $\Delta V$ detected at the above-described step S302 is not less than a predetermined threshold Vth. The threshold Vth is set based on a voltage variation that is to be originally achieved during the applied voltage operation. The Vth can then be set at about "original voltage variation×0.9." If the relation of $\Delta V \geq Vth$ is met, the normal voltage operation is assumed, and proceeding to step S306. Step S306 then calculates the element admittance from the voltage operation amount $\Delta V$ and current variation $\Delta I$ (element admittance=$\Delta I/\Delta V$).

If the relation of $\Delta V<Vth$ is determined in the above-described step S304, the voltage operation amount is assumed to be an abnormal value. Step S305 then performs a guard process of the voltage operation amount $\Delta V$. Step S306 then calculates the element admittance. The guard process in step S305 replaces the voltage operation amount $\Delta V$ with "Vth." Finally, step S307 stores the above-described calculated element admittance in a memory such as RAM as the data for abnormality detection.

FIG. 8 shows a flowchart of the abnormality detection process. This process will replace the process shown in FIG. 5.

In FIG. 8, step S401 reads the element admittance calculated as the data for abnormality detection as shown in FIG. 7. Step S402 then detects the presence or absence of any abnormality in the sensor control system based on the above-described read element admittance. If the element admittance is in a predetermined range, the sensor control system is determined to be normal (step S403).

If the element admittance is not in a predetermined range, the sensor control system is determined to be abnormal (step S404). If, for example, the element admittance is zero or near zero, the sensor control system is determined to be abnormal. Step S405 then determines whether the voltage operation amount $\Delta V$ is an abnormal value, i.e., whether the threshold Vth has replaced the voltage operation amount $\Delta V$, during the admittance calculation. If the voltage operation amount $\Delta V$ is an abnormal value, step S406 then specifies the abnormality as the short-circuit based abnormality such as the power supply short circuit and GND short circuit at each terminal of the sensor element 10. It is because the alternating operation of the applied voltage on the sensor is impossible and the current variation $\Delta I$ is zero, if the power supply short circuit, GND short circuit, or terminal-to-terminal short circuit occurs at each of the terminals T1 and T2 of the sensor element 10. As described above, the second embodiment can suitably detect the short circuit based abnormality in the sensor element 10.

(Modifications)

It should be appreciated that the present invention is not limited to the embodiments described above and may be practiced in other embodiments, for example, as follows.

The first embodiment described above detects the abnormality in the sensor control system based on the current variation ΔI during the detection of the impedance. Alternatively, the abnormality in the sensor control system may be detected based on the element current measured at the output of the operational amplifier 21. In this case, the abnormality is determined to occur in the sensor control system, if the element current measured at the output of the operational amplifier 21 is fixed at or near the boundary value of the operating range of the operational amplifier 21 (such as equivalent to 5 V or near 5V, for 5V drive amplifier).

Figure 9:
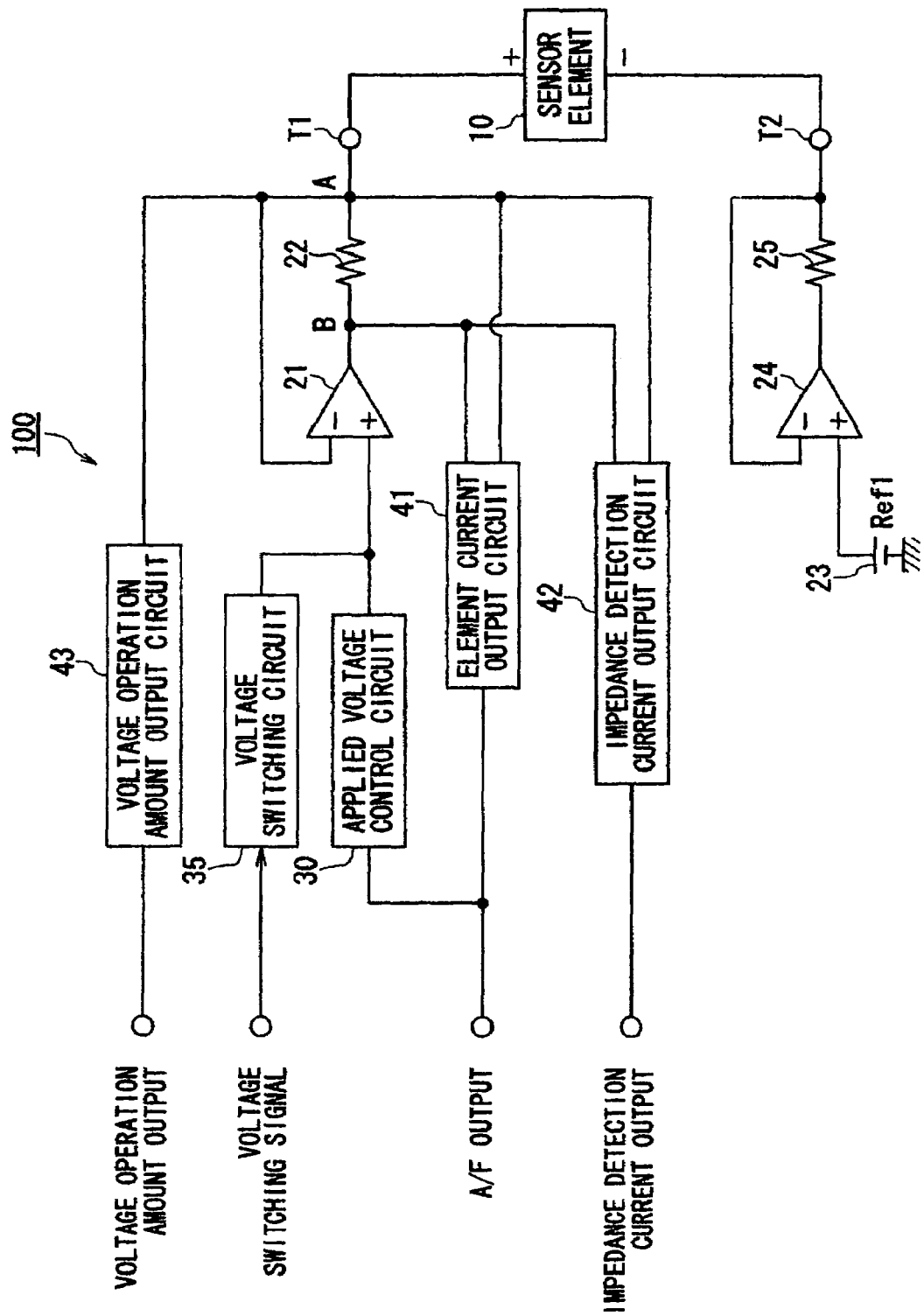
FIG. 9 shows a block diagram of a sensor control circuit in another embodiment.
Figure 10:
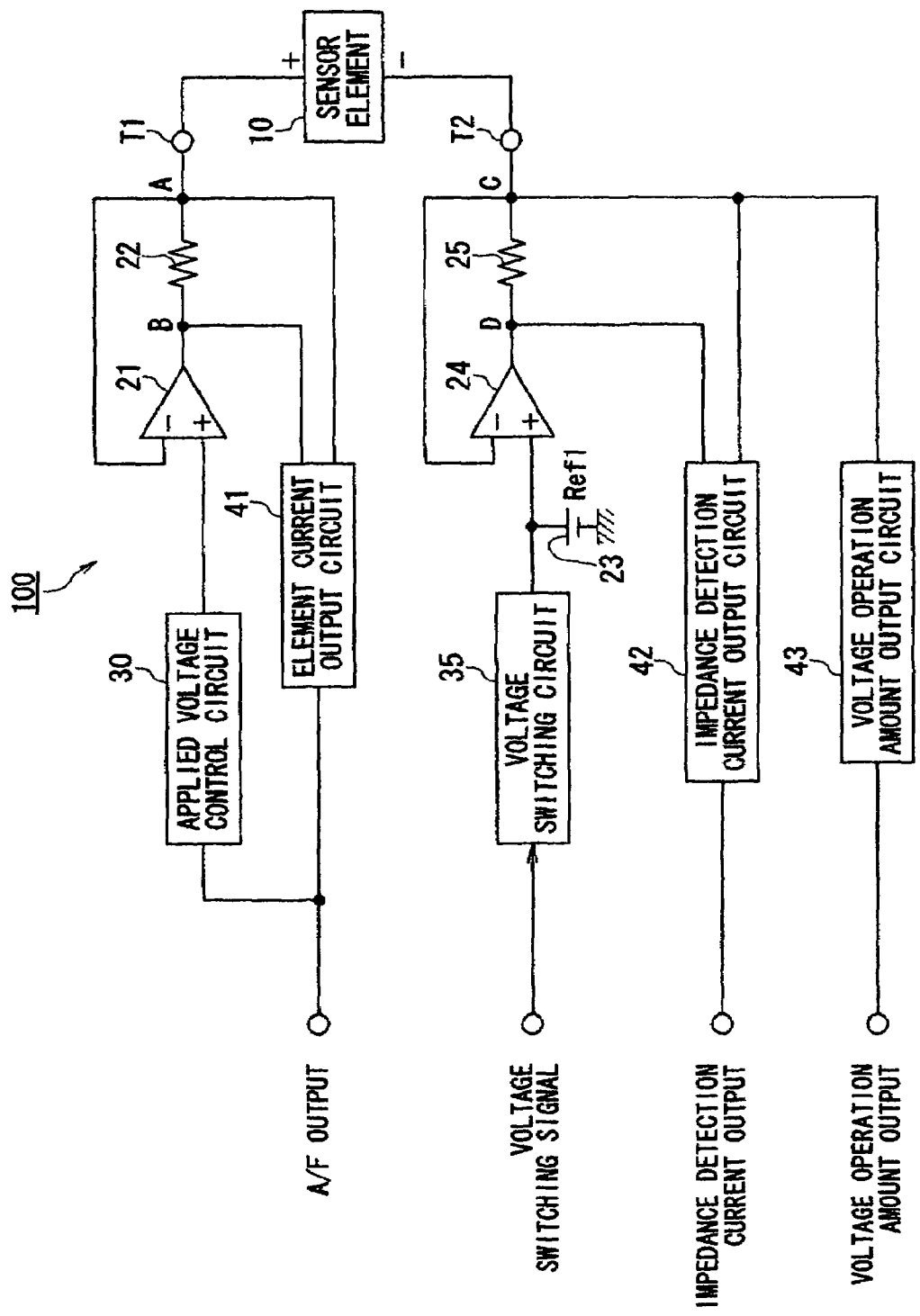
FIG. 10 shows a block diagram of a sensor control circuit in another embodiment.

The configuration of the sensor control system 100 can be modified as shown in FIGS. 9 and 10. The configuration in FIG. 9 differs from that in FIG. 1 in that it includes on the + terminal T1 side of the sensor element 10 the applied voltage control circuit 30 and the voltage switching circuit 35, and includes on the − terminal T2 side the reference power supply 23. On the + terminal T1 side, the element current output circuit 41 and the impedance detection current output circuit 42, including such as the differential amplifier, are connected across the terminals A and B of the current detection resistance 22. The outputs of the element current output circuit 41 and impedance detection current output circuit 42 are the A/F output and impedance detection current output, respectively. The voltage operation amount output circuit 43 receives the point A voltage. The output of the circuit 43 is the voltage operation amount output. The above-described configuration can also detect the abnormality in the sensor control system based on the impedance detection current output.

The configuration in FIG. 10 differs from that in FIG. 1 in that it includes on the + terminal T1 side of the sensor element 10 the applied voltage control circuit 30. Also on the + terminal T1 side, the element current output circuit 41 connects across the terminals A and B of the current detection resistance 22. The output of the element current output circuit 41 is the A/F output. On the − terminal T2 side of the sensor element 10, the reference power supply 23 and voltage switching circuit 35 reside. Also on the − terminal T2 side, the impedance detection current output circuit 42 connects across the terminals C and D of the current detection resistance 22. The output of the impedance detection current output circuit 42 is the impedance detection current output. The voltage operation amount output circuit 43 receives the point C voltage. The output of the circuit 43 is the voltage operation amount output. The above-described configuration can also detect the abnormality in the sensor control system based on the impedance detection current output.

The embodiments described above use, as the data for abnormality detection, the current variation ΔI (impedance detection current output) responding to the switching of the applied voltage on the sensor, or the detected value of the element admittance. Alternatively, the voltage operation amount ΔV measured during the detection of the element impedance can be used as the data for abnormality detection. It is impossible to provide the normal alternating change of the applied voltage on the sensor or the normal measurement of the voltage operation amount ΔV during the detection of the element impedance, if any abnormality occurs in the sensor control system, such as the power supply short circuit or the GND short circuit at one or both of the + and − terminals of the sensor element 10, or the terminal-to-terminal short circuit across the positive and negative terminals. This fact can lead to the detection of the abnormality in the sensor control system. It may be preferable that the abnormality is determined to occur in the sensor control system when the voltage operation amount ΔV is zero or near zero. It may also be preferable that the abnormality is determined to occur when the voltage operation amount ΔV is less than the variation that is output from the voltage switching circuit 35.

Alternatively, it may be preferable that the abnormality is determined to occur in the sensor control system when the voltage measured at the output of the feedback amplification circuit (e.g., operational amplifier 21) during switching the applied voltage on the sensor is fixed at or near the boundary value of the operating range of the feedback amplification circuit.

The embodiments described above calculate the element impedance (or element admittance) by alternately changing the applied voltage on the sensor and measuring the induced current response. Alternatively, the calculation can be done by alternately changing the sensor element current and measuring the induced voltage response.

Figure 11:
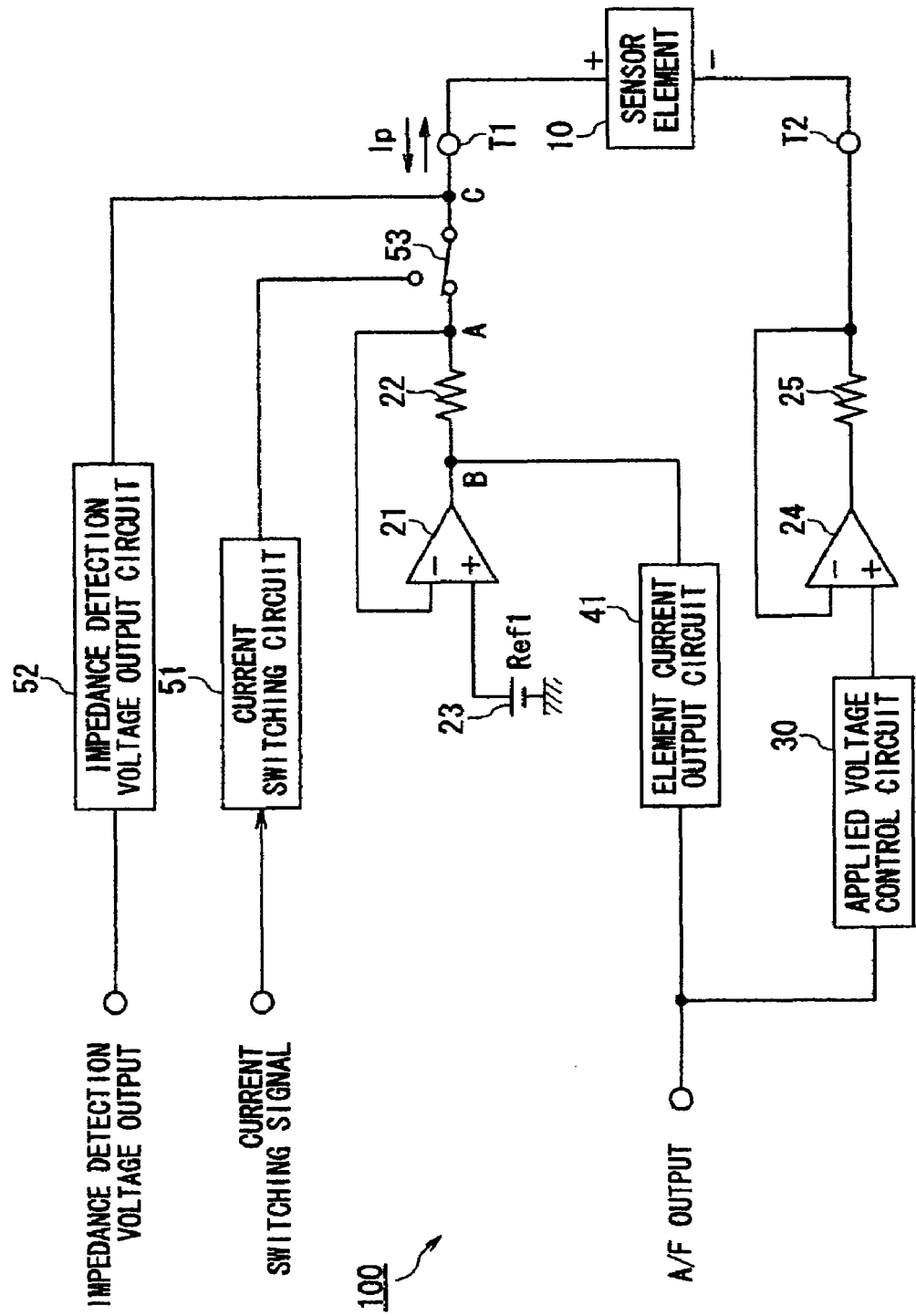
FIG. 11 shows a block diagram of a sensor control circuit in another embodiment.

The configuration for this will be described with reference to FIG. 11. The configuration in FIG. 11 differs from that in FIG. 1 in that a switch circuit 53 connects to the + terminal T1 of the sensor element 10, the current detection resistance 22 connects to one of the switch terminals of the switch circuit 53, and the current switching circuit 51 connects to the other switch terminal. This current switching circuit 51 alternately changes the element current based on the current switching signal that is output from the microcomputer or the like during the calculation of the element impedance. An impedance detection voltage output circuit 52 connects to the point C. The output of this impedance detection voltage output circuit 52 is an impedance detection voltage output. The above-described configuration monitors the voltage change (impedance detection voltage output) responding to the current change, which is measured during the calculation of the element impedance.

The voltage change monitored can be used as a basis to detect the abnormality in the sensor control system. Specifically, no voltage responds to the current change during the detection of the element impedance, if any abnormality occurs in the sensor control system, such as the power supply short circuit or the GND short circuit at one or more of the + and − terminals of the sensor element 10, or the terminal-to-terminal short circuit across the positive and negative terminals. This fact can lead to the detection of the abnormality in the sensor control system. In addition, the calculated value of the element impedance or the measure of the element current, which is obtained during alternately changing the sensor element current, also allows the detection of the abnormality in the sensor control system.

If the short-circuit based abnormality occurs, the output of the impedance detection current output circuit 32 in FIG. 1, for example, does not change, so that the A/D input of the microcomputer 220 does not change. No change of the A/D input also allows the detection of the abnormality in the sensor control system.

The above embodiments have described the A/F sensor with the sensor element structure in FIG. 2. The present invention can also apply to the A/F sensor with other sensor element structures. For example, in addition to the A/F sensor with one layer of the solid electrolyte member, the present invention applies to the A/F sensor with two layers of the solid electrolyte member, or three layers of the solid electrolyte member. Also besides the A/F sensor of the laminated structure, the present invention applies to the A/F sensor of a cup-shaped structure. The present invention also applies to the so-called $O_2$ sensor, which generates the electromotive force across the sensor-element electrodes corresponding to the oxygen concentration in the exhaust gas.

Figure 12:
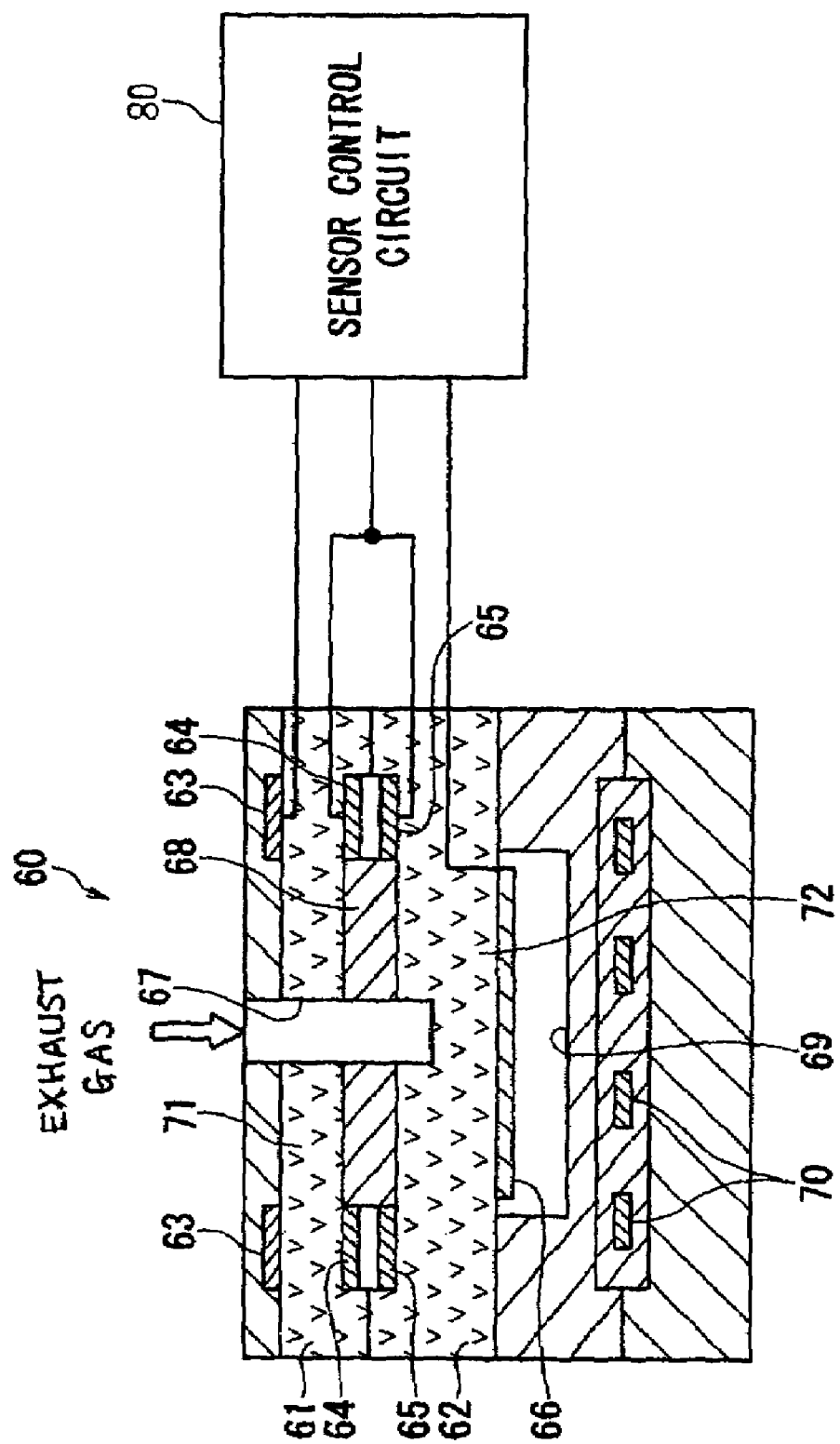
FIG. 12 shows a cross-sectional view of the configuration of another sensor element.

Illustrative examples of other sensors will be described below. FIG. 12 shows a sensor 60 with two layers of the solid electrolyte 61, 62. One solid electrolyte 61 includes a pair of electrodes 63, 64 opposed on each side of it. The other solid electrolyte 62 includes a pair of electrodes 65 and 66 opposed on each side of it. The electrodes 63 to 65 each appear symmetrically at two places in FIG. 12. Each two symmetrical electrodes, however, are connected at any region located perpendicular to the plane of FIG. 12 to make up a single electrode. In the sensor element 60, a pump cell 71 includes the solid electrolyte 61 and the electrodes 63, 64, and an oxygen-sensing cell 72 includes the solid electrolyte 62 and the electrodes 65 and 66. Each of the electrodes 63 to 66 connects to the sensor control system 80. The sensor element 60 has the laminated structure as in the above-described sensor element 10. In FIG. 12, a reference 67 denotes a gas introduction hole, a reference 68 does a porous diffusion layer, a reference 69 does an atmosphere duct, and a symbol 70 does a heater. The oxygen-sensing cell 72 is also generally referred to as an electromotive force cell or an oxygen concentration detection cell.

In the A/F sensors with the above-described sensor element structure, the oxygen-sensing cell 72 generates two values (0 V or 0.9 V) of an electromotive force output depending on whether the exhaust gas is lean or rich with respect to the stoichiometry. For a lean exhaust gas, for example, the oxygen-sensing cell 72 will generate a lower electromotive force output. In contrast, for a rich exhaust gas, the oxygen-sensing cell 72 will generate a higher electromotive force output. In this case, the sensor control circuit 80 controls the applied voltage to the pump cell 71 in such a way that the oxygen-sensing cell 72 generates the electromotive force of the stoichiometry value (0.45V).

Figure 13:
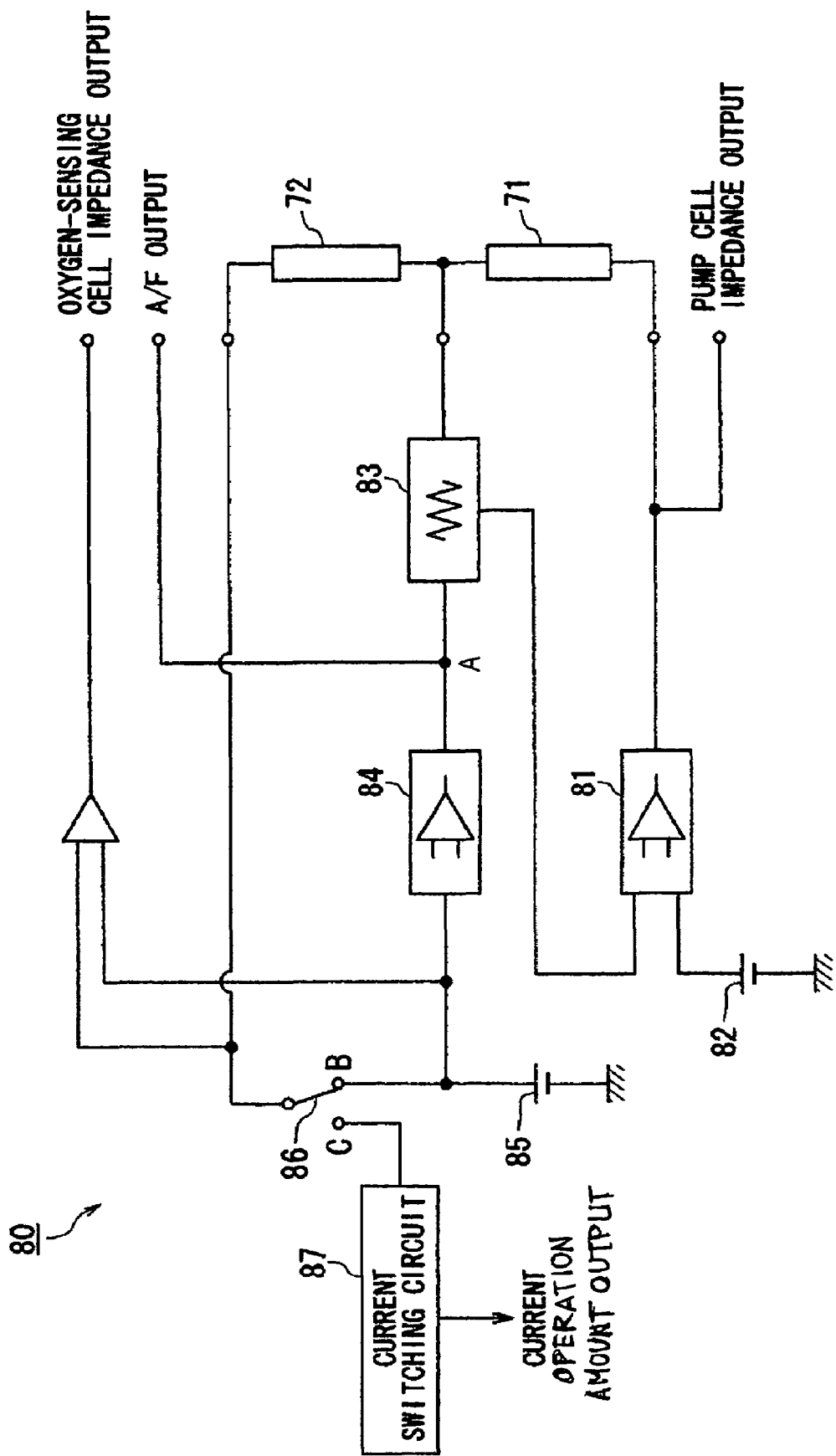
FIG. 13 shows a block diagram of a sensor control circuit in another embodiment.

FIG. 13 shows the configuration of the sensor control circuit 80. This circuit example can operate the current flow through the oxygen-sensing cell 72 to both the positive and negative sides. The terminal voltage of the pump cell 71 and oxygen-sensing cell 72 enables the calculation of the element impedance of a pump cell 71 and the oxygen-sensing cell 72, respectively.

In FIG. 13, an operational amplifier 81 connects to one of the terminals (electrode 63 in FIG. 12) of the pump cell 71. To the operational amplifier 81 are connected a reference-voltage generation portion 82 for generating the reference voltage and an electromotive force detection portion 83 for detecting the electromotive force of the oxygen-sensing cell 72. In this case, the sensor control circuit 80 controls the current flow through the pump cell 71 (pump cell current) to provide a constant electromotive force (0.45 V) of the oxygen-sensing cell 72. The pump cell current changes the voltage at point A in FIG. 13, which is output as the A/F detected value. This is able to provide the A/F output that corresponds to the present oxygen concentration in the exhaust gas (air-fuel ratio).

An operational amplifier 84, together with a capacitor 85, forms a sample hold circuit. The circuit can store and hold the electromotive force of the oxygen-sensing cell 72 right before detecting the impedance of the oxygen-sensing cell 72. A switch circuit 86 switches the circuit between the normal state of detecting oxygen concentration and the state of detecting element impedance. Connecting to point B as shown in FIG. 13 can detect the electromotive force of the oxygen-sensing cell 72 to provide the A/F output that corresponds to the oxygen concentration in the exhaust gas, as described above. Switching to point C can provide the oxygen-sensing cell 72 with the alternate changing current from a current switching circuit 87. The current switching circuit 87 can output a constant current of both positive and negative polarity. The circuit 87 can alternately switch the current at a frequency of about a few kilo-hertzs. The current operation amount of the current switching circuit 87 is detected as the current operation amount output.

With the switch circuit 86 switched to point C, the terminal voltage of the pump cell 71 is sensed as the pump cell impedance output and the terminal voltage of the oxygen-sensing cell 72 is sensed as the oxygen-sensing cell impedance output. The terminal voltage of the pump cell 71 and the current operation amount of the current switching circuit 87 then allow the calculation of the element impedance of the pump cell 71. The terminal voltage of the oxygen-sensing cell 72 and the current operation amount of the current switching circuit 87 allow the calculation of the element impedance of the oxygen-sensing cell 72.

In the above-described configurations, if, for example, the power supply short circuit occurs at one or both of the terminals of the pump cell 71 or oxygen-sensing cell 72, no terminal voltage will change because the power supply provides a current greater in value than the current switching circuit 87 can operate. In this case, the current operation amount is modified to a predetermined value and the modified value is used to calculate the element impedance. The element impedance calculated will be a value apparently lower than usual. This calculated value allows the determination that abnormality occurs in the sensor control system. The current operation amount modified to a predetermined value allows the determination that the abnormality is the short circuit based abnormality. In addition, the abnormality can also be detected when the GND short circuit or the terminal-to-terminal short circuit occurs at one or both of the terminals of the pump cell 71 or the terminals of the oxygen-sensing cell 72.

As described above, the combination of the sensor element with the configuration shown in FIG. 12 and sensor control circuit with the configuration shown in FIG. 13 can also suitably detect the short circuit based abnormality at each terminal of the sensor element.

Figure 14:
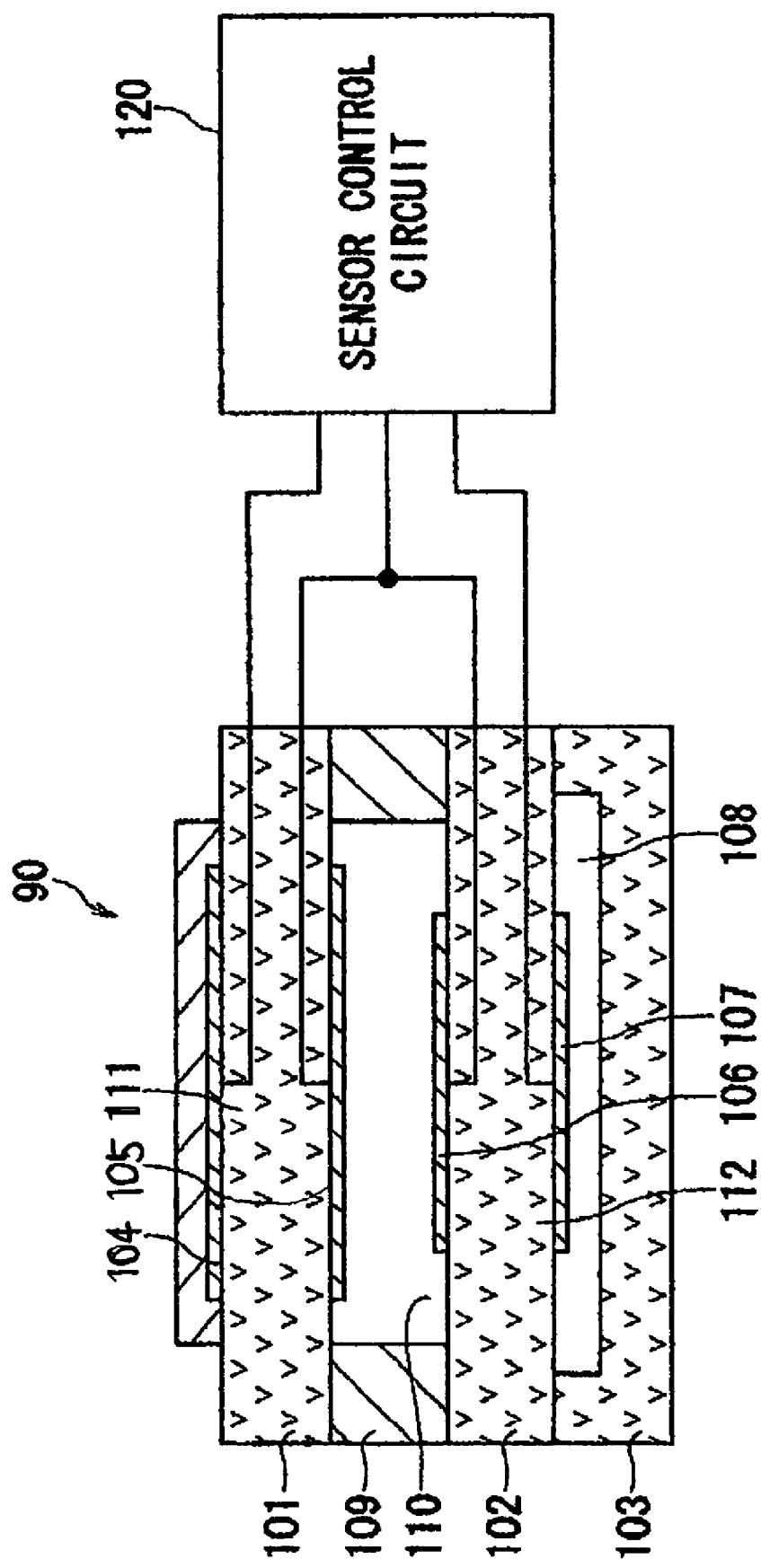
FIG. 14 shows a cross-sectional view of the configuration of another sensor element.

The sensor element may also have the structure shown in FIG. 14. FIG. 14 shows a sensor element 90, which includes three layers of the solid electrolyte 101, 102 and 103. The solid electrolyte 101 includes a pair of electrodes 104 and 105 opposed on each side of it. The solid electrolyte 102 includes a pair of electrodes 106 and 107 opposed on each side of it. In the sensor element 90, a pump cell 111 includes the solid electrolyte 101 and the electrodes 104 and 105, and an oxygen-sensing cell 112 includes the solid electrolyte 102 and the electrodes 102 and 107. The solid electrolyte 103 forms the wall material to secure the oxygen reference chamber 108. The sensor element 90 has the laminated structure as in the above-described sensor element 10 or the like. In FIG. 14, a reference 109 denotes a porous diffusion layer and a reference 110 does a gas detection chamber. The oxygen-sensing cell 112 is also generally referred to as an electromotive force cell or an oxygen concentration detection cell, as in the above-described oxygen-sensing cell 72 in FIG. 12. The circuitry for the sensor element 90 is generally the same as shown in FIG. 13, the description of which is then omitted here.

Figure 15:
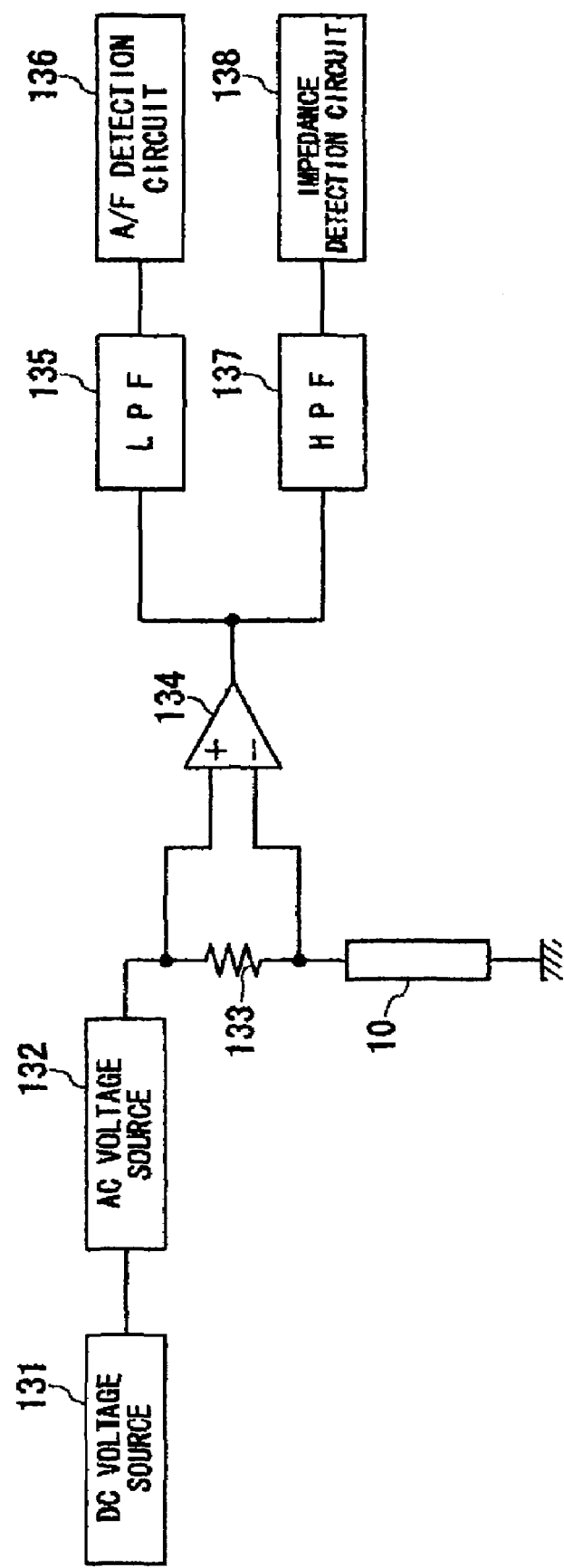
FIG. 15 shows a block diagram of a sensor control circuit in another embodiment.

FIG. 15 shows a configuration example of a sensor control circuit that continuously applies the alternating voltage to the sensor element to detect the impedance. A series circuit of a DC voltage source 131, an AC voltage source 132, and a resistance 133 connects to the sensor element 10. Both terminals of the resistance 133 connect to the input terminals of a differential amplifier 134. The output terminals of the differential amplifier 134 connect to an LPF (low pass filter) 135 and an HPF (high pass filter) 137. The LPF 135 removes the AC component from the detection signal across the resistance 133. The LPF thus extracts the signal component that corresponds to the oxygen concentration (air-fuel ratio) in the exhaust gas and outputs the signal to the A/F detection circuit 136. The A/F detection circuit 136 then detects the oxygen concentration from the signal after the LPF. The HPF 137 extracts only the AC component from the detection signal across the resistance 133. The HPF 137 then outputs this extracted signal to the impedance detection circuit 138. The impedance detection circuit 138 detects the element impedance from the signal after the HPF.

The sensor control circuit with the configuration shown in FIG. 15 can also suitably detect the short circuit based abnormality at each terminal of the sensor element by monitoring the variation on the voltage operation side and the responsive variation on the response side.

The $O_2$ sensor will include, for example, an applied voltage (or current) switching circuit on one terminal side of the sensor element. The sensor will also include a detection circuit of the current variation (or voltage variation) caused by the switched applied voltage (or current), which the circuit is provided on the other terminal side. The operation signal of the applied voltage (or current) and the responsive response signal may preferably allow the calculation of the element impedance and the detection of the abnormality in the sensor control system.

In addition to the A/F sensor for detecting the oxygen concentration, the present invention also applies to gas concentration sensors for detecting other components concentrations. A multiple-type gas concentration sensor, for example, includes a plurality of cells made of solid electrolyte member. Of the cells, the first cell (pump cell) exhausts or draws the oxygen in the detected gas and detects the oxygen concentration. The second cell (sensor cell) detects the specific component concentration in the oxygen-exhausted gas. This gas sensor can be embodied, for example, as a $NO_x$ sensor for detecting the $NO_x$ concentration in the exhaust gas. The present invention also applies to the $NO_x$ sensor to suitably detect the abnormality in the sensor control system. In this case, the element impedance may preferably be detected for any cell such as the first cell and second cell. The gas concentration sensor may include a plurality of cells including, in addition to the above-described first and second cells, the third cell (monitor cell or second pump cell) for detecting the remaining oxygen concentration in the oxygen-exhausted gas.

In addition to the gas concentration sensor that can detect the $NO_x$ concentration, the present invention applies to gas concentration sensors that can detect other specific components concentrations such as HC concentration or CO concentration. In this case, the pump cell exhausts the extra oxygen in the detected gas, and the sensor cell decomposes HC or CO in the extra-oxygen-exhausted gas to detect the HC concentration or CO concentration. The present invention can also be used for gas concentration detecting apparatuses other than for automobiles, and can also detect gases other than the exhaust gas.

The present invention may be embodied in other specific forms without departing from the spirit or essential characteristics thereof. The foregoing embodiments and modifications are therefore to be considered in all respects as illustrative and not restrictive, the scope of the present invention being indicated by the appended claims rather than by the foregoing description and all changes which come within the meaning and range of equivalency of the claims are therefore intended to be embraced therein.

The entire disclosure of Japanese Patent Application Nos. 2003-96375 filed on Mar. 31, 2003 and 2004-39566 filed on Feb. 17, 2004 including the specification, claims, drawings and summary are incorporated herein by reference in its entirety.

What is claimed is:

1. A gas concentration detecting apparatus applied to a gas concentration sensor including a sensor element sensing a concentration of a gas to be detected, the sensor element being equipped with a solid electrolyte member and one or more pairs of electrodes disposed on the solid electrolyte member, the apparatus comprising:

a control unit configured to control a voltage applied to at least one of positive and negative terminals connected to the electrodes of the sensor element;

a measurement unit configured to measure either an element current flow caused by the applied voltage corresponding to a concentration of a specific component of the gas, every time the voltage is applied under the control of the applied voltage, or an electromotive force generated between the electrodes of the sensor element corresponding to the concentration of the specific component of the gas, every time the voltage is applied under the control of the applied voltage;

a change causing unit configured to cause a change in either the applied voltage to the sensor element or the element current through the sensor element;

a change amount measuring unit configured to measure an amount of a change in each of a current value and a voltage value caused in response to the change caused in either the applied voltage or the element current;

a calculation unit configured to calculate an amount of a resistance component to resist the element current flow through the sensor element on the basis of a ratio between the amounts of the changes in the current value and the voltage value; and a detection unit configured to detect abnormality relating to controlling the sensor by utilizing information relating to the amount of the resistance component calculated by the calculation unit, the information being at least one of the amounts of the changes in the current value and the voltage value, wherein the detection unit comprises a monitor unit configured to monitor the measured amount of the change in either the current value or the voltage value; and a determination unit configured to determine occurrence of the abnormality on the basis of the amount of the change monitored by the monitor unit, when the amount of the change in either the current value or the voltage value is equal to zero or a value substantially regarded as zero.

2. A gas concentration detecting apparatus applied to a gas concentration sensor including a sensor element sensing a concentration of a gas to be detected, the sensor element being equipped with a solid electrolyte member and one or more pairs of electrodes disposed on the solid electrolyte member, the apparatus comprising:

a control unit configured to control a voltage applied to at least one of positive and negative terminals connected to the electrodes of the sensor element;

a measurement unit configured to measure either an element current flow caused by the applied voltage corresponding to a concentration of a specific component of the gas, every time the voltage is applied under the control of the applied voltage, or an electromotive force generated between the electrodes of the sensor element corresponding to the concentration of the specific component of the gas, every time the voltage is applied under the control of the applied voltage;

a change causing unit configured to cause a change in either the applied voltage to the sensor element or the element current through the sensor element;

a change amount measuring unit configured to measure an amount of a change in each of a current value and a voltage value caused in response to the change caused in either the applied voltage or the element current;

a calculation unit configured to calculate an amount of a resistance component to resist the element current flow through the sensor element on the basis of a ratio between the amounts of the changes in the current value and the voltage value; and a detection unit configured to detect abnormality relating to controlling the sensor by utilizing information relating to the amount of the resistance component calculated by the calculation unit, the information being at least one of the amounts of the changes in the current value and the voltage value;

wherein the detection unit is provided with a monitor unit configured to monitor the amount of the change in either the current value or the voltage value, the amount of the change being measured by the measurement unit, and a determination unit configured to determine the abnormality on the basis of the amount of the change monitored by the monitor unit;

the control unit is provided with a feedback amplifying circuit connected to the positive terminal and the negative terminal of the sensor element, the voltage being applied to the sensor element via the feedback amplifying circuit;

the measurement unit is configured to measure either the current value or the voltage value in response to the change caused in either the applied voltage or the element current at a position on an output side of the feedback amplifying circuit; and the determination unit is configured to determine that there occurs the abnormality, when either the current value or the voltage value measured at the position on the output side of the feedback amplifying circuit is fixed at a boundary value or thereabouts of a range in which the feedback amplifying circuit operates.

3. The gas concentration detecting apparatus according to claim 2, wherein the feedback amplifying circuit has a function of limiting an output of the feedback amplifying circuit into a predetermined range.

4. A gas concentration detecting apparatus applied to a gas concentration sensor including a sensor element sensing a concentration of a gas to be detected, the sensor element being equipped with a solid electrolyte member and one or more pairs of electrodes disposed on the solid electrolyte member, the apparatus comprising:

a control unit configured to control a voltage applied to at least one of positive and negative terminals connected to the electrodes of the sensor element;

a measurement unit configured to measure either an element current flow caused by the applied voltage corresponding to a concentration of a specific component of the gas, every time the voltage is applied under the control of the applied voltage, or an electromotive force generated between the electrodes of the sensor element corresponding to the concentration of the specific component of the gas, every time the voltage is applied under the control of the applied voltage;

a change causing unit configured to cause a change in either the applied voltage to the sensor element or the element current through the sensor element;

a change amount measuring unit configured to measure an amount of a change in each of a current value and a voltage value caused in response to the change caused in either the applied voltage or the element current;

a calculation unit configured to calculate an amount of a resistance component to resist the element current flow through the sensor element on the basis of a ratio between the amounts of the changes in the current value and the voltage value; and a detection unit configured to detect abnormality relating to control of the sensor by utilizing information relating to the amount of the resistance component calculated by the calculation unit;

wherein the change amount measuring unit includes an operated amount measuring unit configured to measure an actually operated amount of either the applied voltage or the sensor current when the change is caused in the either the applied voltage or the sensor current and the detection unit includes a determination unit configured to determine whether or not the actually operated amount is abnormal; and a processing unit configured to change the actually operated amount to a predetermined value, to calculate an amount of the resistance component by using the predetermined value of the actually operate amount, and to detect abnormality relating to controlling the sensor based on the amount of the resistance component resulting from the predetermined value of the actually operate amount.

5. The gas concentration detecting apparatus according to claim 4, wherein the determination unit includes a unit that determines that the actually operated amount is abnormal, provided that the actually operated amount is lower than a predetermined threshold; and the processing unit includes a unit that changes the actually operated amount to the predetermined value in cases where the determination unit determines that the actually operated amount is abnormal.

6. The gas concentration detecting apparatus according to claim 5, comprising a unit that determines that there occurs abnormality relating to short circuit in the terminals of the sensor element, when the abnormality relating to controlling the sensor is detected and the actually operated amount is abnormal.

7. The gas concentration detecting apparatus according to claim 4, wherein the control unit comprises a feedback amplifying circuit connected to the positive terminal and the negative terminal of the sensor element, the voltage being applied to the sensor element via the feedback amplifying circuit, the measurement unit that measures either the current value or the voltage value in response to the change caused in either the applied voltage or the element current at a position on an output side of the feedback amplifying circuit, wherein the feedback amplifying circuit has a function of limiting an output of the feedback amplifying circuit into a predetermined range.

8. A gas concentration detecting apparatus applied to a gas concentration sensor including a sensor element sensing a concentration of a gas to be detected, the sensor element being equipped with a solid electrolyte member and one or more pairs of electrodes disposed on the solid electrolyte member, the apparatus comprising:

a control unit configured to control a voltage applied to at least one of positive and negative terminals connected to the electrodes of the sensor element;

a measurement unit configured to measure either an element current flow caused by the applied voltage corresponding to a concentration of a specific component of the gas, every time the voltage is applied under the control of the applied voltage, or an electromotive force generated between the electrodes of the sensor element corresponding to the concentration of the specific component of the gas, every time the voltage is applied under the control of the applied voltage;

a change causing unit configured to cause a change in either the applied voltage to the sensor element or the element current through the sensor element;

a change amount measuring unit configured to measure an amount of a change in each of a current value and a voltage value caused in response to the change caused in either the applied voltage or the element current;

a calculation unit configured to calculate an amount of a resistance component to resist the element current flow through the sensor element on the basis of a ratio between the amounts of the changes in the current value and the voltage value; and a detection unit configured to detect abnormality relating to control of the sensor by utilizing information relating to the amount of the resistance component calculated by the calculation unit, wherein the change amount measuring unit includes an operated amount measuring unit that measures an actually operated amount of either the applied voltage or the sensor current obtained when the change is caused in the either the applied voltage or the sensor current, the actually operated amount serving as the information relating to calculating the amount of the resistance component and serving as the amount of the change in one of the current value and the voltage value; and the detection unit includes a determination unit that determines that there occurs the abnormality, when the actually operated amount is zero or a value substantially regarded as being zero.

9. A gas concentration detecting apparatus applied to a gas concentration sensor including a sensor element sensing a concentration of a gas to be detected, the sensor element being equipped with a solid electrolyte member and one or more pairs of electrodes disposed on the solid electrolyte member, the apparatus comprising:

a control unit configured to control a voltage applied to at least one of positive and negative terminals connected to the electrodes of the sensor element;

a measurement unit configured to measure either an element current flow caused by the applied voltage corresponding to a concentration of a specific component of the gas, every time the voltage is applied under the control of the applied voltage, or an electromotive force generated between the electrodes of the sensor element corresponding to the concentration of the specific component of the gas, every time the voltage is applied under the control of the applied voltage;

a change causing unit configured to cause a change in either the applied voltage to the sensor element or the element current through the sensor element;

a change amount measuring unit configured to measure an amount of a change in each of a current value and a voltage value caused in response to the change caused in either the applied voltage or the element current;

a calculation unit configured to calculate an amount of a resistance component to resist the element current flow through the sensor element on the basis of a ratio between the amounts of the changes in the current value and the voltage value; and a detection unit configured to detect abnormality relating to control of the sensor by utilizing information relating to the amount of the resistance component calculated by the calculation unit;

wherein the change amount measuring unit includes an operated amount measuring unit that measures an actually operated amount of either the applied voltage or the sensor current obtained when the change is caused in the either the applied voltage or the sensor current, the actually operated amount serving as the information relating to calculation of the amount of the resistance component and serving as the amount of the change in one of the current value and the voltage value;

the detection unit detects the abnormality with reference to the actually operated amount;

the control unit includes a feedback amplifying circuit connected to the positive terminal and the negative terminal of the sensor element, the voltage being applied to the sensor element via the feedback amplifying circuit;

the measurement unit measures either the current value or the voltage value in response to the change caused in either the applied voltage or the element current at a position on an output side of the feedback amplifying circuit; and the determination unit determines that there occurs the abnormality, when either the current value or the voltage value measured at the position on the output side of the feedback amplifying circuit is fixed at a boundary value or thereabouts of a range in which the feedback amplifying circuit operates.

* * * * *